(12) United States Patent
Sharif

(10) Patent No.: US 6,500,831 B1
(45) Date of Patent: Dec. 31, 2002

(54) NON-PEPTIDE BRADYKININ RECEPTOR ANTAGONISTS FOR USE IN CONTROLLING INTRAOCULAR PRESSURE AND TREATING GLAUCOMA

(75) Inventor: Najam A. Sharif, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/647,571

(22) PCT Filed: Mar. 4, 1999

(86) PCT No.: PCT/US99/04865

§ 371 (c)(1),
(2), (4) Date: Oct. 2, 2000

(87) PCT Pub. No.: WO99/51235

PCT Pub. Date: Oct. 14, 1999

Related U.S. Application Data

(60) Provisional application No. 60/080,730, filed on Apr. 3, 1998.

(51) Int. Cl.[7] .................................................. A61K 31/50
(52) U.S. Cl. .................................. 514/253.06; 514/913
(58) Field of Search .............................. 514/253.06, 913

(56) References Cited

FOREIGN PATENT DOCUMENTS

EP          0 529 499 A1        8/1992

OTHER PUBLICATIONS

Regoli, et al., "Pharmacology of Bradykinin and Related Kinins," *Pharmacological Reviews*, vol. 32:1–46; 1980.
Hall, Judith M., "Bradykinin Receptors: Pharmacological Properties and Biological Roles," *Pharmac. Therapy*, vol. 56:131–190; 1992.
Sharma, J.N., "Therapeutic Prospects of Bradykinin Receptor Antagonists," *Gen. Pharmac.*, vol. 24(2):267–274, 1993.
Ma, et al., "Expression and Cellular Localization of the Kallikrein–Kinin System in Human Ocular Tissues," *Exp. Eye Research*, vol. 63:19–26, 1996.
Regoli, et al., "New Selective Bradykinin Receptor Antagonists and Bradykinin $B_2$ Receptor Characterization," *Trends in Pharmacol. Science*, vol. 11:156–161, Apr. 1990.
Cole, et al., "Action of Bradykinin on Intraocular Pressure and Pupillary Diameter," *Ophthalmology Research*, vol. 6:308–314, 1974.
Llobet, et al., "Effects of Substance P. Bradykinin, Neuropeptide Y, Metenkephalin and $PGE_2$ on Outflow Facility (C) in Bovine Anterior Segments in vitro," *Investigative Ophthalmology & Visual Science*, vol. 37(3), Abstract 953, Feb. 1996.
Sharif, et al., "Pharmacological Characterization of Bradykinin Receptors Coupled to Phosphoinositide Turnover in SV–40 Immortalized Human Trabecular Meshwork Cells," *Exp. Eye Research*, vol. 63:631–637, 1996.

Abe, et al., "A Novel Class of Orally Active Non–Peptide Bradykinin $B_2$ Receptor Antagonists. 1. Construction of the Basic Framework," *Journal Medicinal Chemistry*, vol. 41(4):564–578, 1998.
Salvino, et al., "Design of Potent Non–Peptide Competitive Antagonists of the Human Bradykinin $B_2$ Receptor," *Journal Medicinal Chemistry*, vol. 36(17):2583–2584, 1993.
Cheronis, et al., "Design, Synthesis, and in vitro Activity of Bis(succinimido)hexane Peptide Heterodimers with Combined $B_1$ and $B_2$ Antagonist Activity[1,2]", *Journal Medicinal Chemistry*, vol. 37(3):348–355, 1994.
Cheronis, et al., "A New Class of Bradykinin Antagonists: Synthesis and in vitro Activity of Bissuccinimidoalkane Peptide Dimers[1,2]," *Journal Medicinal Chemistry*, vol. 35(9):1563–1572, 1992.
Srivastava, et al., "Hybrid Peptides Having Mixed Substance P (NK1), Neurokinin A (NK2) and Bradykinin (BK2) Antagonist Properties," *Immunopharmacology*, vol. 33:194–196, 1996.
Mavunkel, et al., "Synthesis and Characterization of Pseudopeptide Bradykinin B2 Receptor Antagonists Containing the 1,3,8–Triazaspiro[4.5]decan–4–one Ring System," *J. Medicinal Chemistry*, vol. 39(16):3169–3173, 1996.
Sharif, et al., "The Neuropeptide Bradykinin Stimulates Phosphoinositide Turnover in HSDM1C1 Cells: $B_2$–Antagonist–Sensitive Responses and Receptor Binding Studies," *Neurochemical Research*, vol. 18(12):1313–1320, 1993.
Sharif, et al., "Identification of $B_2$–Bradykinin Receptors in Guinea Pig Brain Regions, Spinal Cord and Peripheral Tissues," *Neurochemical International*, vol. 18(1):89–96, 1991.
Berridge, et al., "Lithium Amplifies Agonist–Dependent Phosphatidylinositol Responses In Brain and Salivary Glands," *Biochem J.*, vol. 206:587–595, 1982.
Llobet, et al., "Bradykinin Decreases Outflow Facility in Perfused Anterior Segments and Induces Shape Changes in Passaged BTM Cells a in vitro," *Investigative Ophthalmology & Visual Science*, vol. 40(1):113–125, Jan., 1999.
Yokoyama, et al., "Implication of Polymodal Receptor Activities in Intraocular Pressure Elevation by Neurogenic Inflammation," *Japanese Journal of Ophthalmology*, vol. 34(2):245–255, 1990.
Kaufman, et al., "Effect of Serotonin, Histamine and Bradykinin on Outflow Facility Following Ciliary Muscle Retrodisplacement in the Cynomolgus Monkey," *Exp. Eye Research*, vol. 35:191–199, 1982.

(List continued on next page.)

*Primary Examiner*—Zohreh Fay
(74) *Attorney, Agent, or Firm*—Sally Yeager

(57) ABSTRACT

This invention relates to the topical ocular use of non-peptide bradykinin receptor antagonists to treat glaucoma and ocular hypertension.

8 Claims, No Drawings

OTHER PUBLICATIONS

Douty, et al., "Synthesis of Non–peptide Bradykinin $B_2$ Receptor Antagonists," *Bioorganic & Medicinal Chemistry Letters*, vol. 5(4):363–366, 1995.

Hall, et al., "Inhibition of Bradykinin–evoked Trigeminal Nerve Stimulation by the Non–peptide Bradykinin $B^2$ Receptor Antagonist WIN 64338 in vivo and in vitro," *British Journal of Pharmacology*, vol. 116:3164–3168, 1995.

Aramori, et al., "Novel Subtype Selective Nonpeptide Bradykinin Receptor Antagonists FR167344 and FR173657," *Molecular Pharmacology*, vol. 512):171–176, 1997.

Griesbacher, et al., "Effect of Bradykinin Antagonists on Bradykinin–induced Plasma Extravasation, Venoconstriction, Prostaglandin $E_2$ Release, Nociceptor Stimulation and Contraction of the Iris Sphincter Muscle in the Rabbit," *British Journal Pharmac.*, vol. 92:333–340, 1987.

Hingorani, et al., "Therapeutic Options in Ocular Allergic Disease," *Drugs*, vol. 50(2):208–221, 1995.

NON-PEPTIDE BRADYKININ RECEPTOR ANTAGONISTS FOR USE IN CONTROLLING INTRAOCULAR PRESSURE AND TREATING GLAUCOMA

This application is a 371 of PCT/US99/04865 filed Mar. 4, 1999. This application claim benefit to provisional application No. 60/080,730 Apr. 3, 1998.

The present invention relates to the topical ocular use of non-peptide bradykinin receptor antagonists to treat glaucoma and ocular hypertension.

BACKGROUND OF THE INVENTION

Glaucoma is a progressive disease which leads to optic nerve damage and, ultimately, a total loss of vision. The causes of this disease have been the subject of extensive studies for many years, but are still not fully understood. The principal symptom of, and/or risk factor for, the disease is elevated intraocular pressure or ocular hypertension due to excess aqueous humor in the anterior chamber of the eye.

The reasons why aqueous humor accumulates are not fully understood. It is known that elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

The pharmaceutical approaches currently being pursued in the treatment of glaucoma have exhibited various side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis which can affect patient compliance and/or necessitate the withdrawal of treatment. Moreover, some beta-blockers have increasingly become associated with serious pulmonary side effects attributable to their effects on beta-2 receptors in pulmonary tissue. Sympathomimetics cause tachycardia, arrhythmia and hypertension. There is therefore a continuing need for therapies which control the elevated intraocular pressure associated with glaucoma.

Bradykinin or "BK," is an endogenous peptide made up of nine amino acids (i.e., Arg-Pro-Pro-Gly-Phe-Ser-Pro-Phe-Arg). BK is found in many organs, including the eye. BK exhibits many biological effects in the body, including tissue contraction, fluid and ion secretion and pain inducement (Regoli and Barabe, *Pharmacol. Rev.*, volume 32, pages 1–46 (1980) and Hall, *Pharmacol. Ther.*, volume 56, pages 131–190 (1992)).

BK and another endogenous peptide, Lys-BK, bind to two major BK receptor-subtypes. namely $B_1$ and $B_2$, to produce their biological effects. The $B_2$-subtype is found to be expressed under normal physiological conditions, while the $B_1$-subtype is induced during injury or trauma (Regoli, and Barabe, *Pharmacol. Rev.*, and Hall, *Pharmacol. Ther.*). While the $B_1$-subtype has a low affinity for BK and a high affinity for Des-Arg$^9$-BK and Lys-BK, the $B_2$-subtype has a high affinity for BK and Lys-BK but a low affinity for Des-Arg$^9$-BK.

Both receptor subtypes have been cloned and shown to be coupled to G-proteins and phospholipase C, and their activation results in the generation of the second messengers inositol trisphosphate ("IP$_3$") and diacylglycerol ("DAG") (Hall, *Pharmacol. Ther.*). The signal transduction of BK receptor binding results in IP$_3$-stimulated mobilization of intracellular Ca$^{2+}$, followed by DAG phosphorylation of protein kinase C. Together, these events lead to the final biological response, such as tissue contraction or fluid secretion.

The majority of the physiological and pathological effects of BK are mediated by the $B_2$-receptor-subtype. However, recent pharmacological evidence points to two additional BK-receptor subtypes, namely $B_3$ and $B_4$ (Hall, *Pharmacol. Ther.*, and Sharma, *Gen. Pharmacol.*, volume 24, pages 267–274, (1993)). The $B_3$ and $B_4$ receptor subtypes are actually stimulated by certain peptide BK antagonists, whereas the $B_1$ and $B_2$ subtypes are blocked by those antagonists (Sharma, *Gen. Pharmacol.*). While the presence of $B_3$ or $B_4$ receptor subtypes in the eye has not been investigated, it is believed they may be present since there is a robust BK-precursor and BK-generating enzyme pool in human ocular tissues and also the presence of the $B_1$ and $B_2$ receptors (Ma et al., *Exp. Eye Res.*, volume 63, pages 19–26, (1996)).

Most of the previously described BK antagonists have been peptides of limited potency and selectivity (Regoli et al., *Trends in Pharmacol. Sci.*, volume 11, pages 156–161, (1990) and Hall, *Pharmacol. Ther.*). Peptides are labile, highly polar and, therefore, difficult to formulate and deliver to the site of treatment (Sharma, *Gen. Pharmacol.*). Such peptides would be especially difficult to formulate for topical administration to the eye due to the relatively impenetrable thick scleral and corneal/conjunctival covering of the eye.

Nowhere in the art has it been disclosed, taught or suggested to use non-peptide BK antagonists to treat ocular hypertension and glaucoma.

SUMMARY OF THE INVENTION

The present invention is directed to compositions and methods for the treatment of glaucoma and ocular hypertension. More specifically, the present invention is directed to topical ophthalmic compositions containing one or more bradykinin antagonists and methods of treating glaucoma and ocular hypertension.

The compositions and methods of the present invention employ antagonists to bradykinin receptors which are relatively stable and bioavailable to the relevant ocular tissues. As stated above, previous BK antagonists have been peptides and thus labile and of low bioavailability. The present invention compositions and methods, in contrast, are directed to stabile, bioavailable non-peptide BK antagonists. Preferred compositions and methods are directed to bradykinin $B_2$ receptor antagonists.

DETAILED DESCRIPTION OF THE INVENTION

The present invention provides compositions and methods of their use in treating glaucoma and ocular hypertension. More specifically, the present invention is directed to ophthalmic compositions comprising non-peptide bradykinin antagonists and methods of use in treating glaucoma and ocular hypertension.

While applicants do not wish to be bound by any theory, it is believed that BK causes an elevation in IOP by either inhibiting outflow of aqueous humor or increasing the production of aqueous humor. Thus, the administration of BK antagonists to the eye is thought to inhibit BK's receptor action and hence stabilize or lower IOP.

It has been shown that injection of BK in the eyes of animals (e.g., rabbits) causes pupil constriction and increases IOP (Cole and Ungar, *Ophthalmol Res.*, volume 6, pages 308–314 (1974)) by inhibiting the outflow of aqueous humor (Llobet, *Invest. Ophthalmol. Vis. Sci.* (suppl) volume 37, Abstract No. 953 (1996)). As stated above, increased IOP can lead to ocular hypertension, a major risk factor in the etiology of glaucoma.

The trabecular meshwork in the anterior chamber of the eye represents the primary locus for aqueous humor drainage, which apparently regulates IOP ("conventional outflow"). Defects(s) in this filtration system may underlie the etiology of open angle glaucoma. specifically by raising IOP. While the phagocytic action of trabecular meshwork cells appears important, the muscle-like tension in the trabecular meshwork may also contribute to the drainage of the aqueous humor to provide an homeostatic control of IOP. Recently, functional BK $B_2$ receptors have been discovered on the surfaces of human trabecular meshwork cells (Sharif and Xu, *Exp. Eye Res.*, volume 63, pages 631–637 (1996)). Thus, it is believed that BK may aberrantly contract the ciliary muscle and/or the trabecular meshwork, in addition to activating the ciliary epithelium, to produce its IOP-elevating effects.

The actions of BK on the ciliary epithelium to stimulate the production of aqueous humor (i.e., enhance inflow) may also result in IOP elevation. Therefore, the inventors believe that pharmacological agents which block the effects of BK in the anterior chamber will lower IOP and result in ocular hypotension, which in turn would reduce the risk for development of glaucoma.

Bradykinin receptors have been classified into at least four receptor subtypes. These subtypes include $B_1$, $B_2$, $B_3$ and $B_4$. Other subtypes may be elucidated in the future. For purposes of the present invention, all of these subtypes are included in the definition, "bradykinin receptor."

The compositions of the present invention will comprise one or more bradykinin receptor antagonists in a suitable pharmaceutical vehicle. As used herein, a "bradykinin antagonist" or "BK antagonist" refers to a compound of the present invention which inhibits the binding of bradykinin to a bradykinin receptor and therefore prevents activation of the receptor. The BK antagonists of the present invention are selected from various chemical classes, except linear monomeric peptide classes, e.g., HOE 140. Such classes of BK antagonists of the present invention include non-peptide BK-antagonists, cyclic peptides antagonists, peptide dimer antagonists, cyclic organic molecule antagonists, peptidomimetic antagonists, or other classes of BK-antagonists which are not readily hydrolizable, in contrast to linear peptides. As used herein, the term "non-peptide BK antagonist" refers to those BK antagonists which are not linear, monomeric peptides.

Examples of organic non-peptide BK antagonists of the present invention include FR173657 ((E)-3-(6-acetamido-3-pyridyl)-N-[N-[2,4-dichloro-3-[(2-methyl-8-quinolinyl)oxymethyl]phenyl]-N-methylaminocarbonylmethyl] acrylamide); FR167344 (N-[N-[3-[3-bromo-2-methylimdazo[1,2-a]pyridin-8-yl)oxymethyl]2,4-dichlorophenyl]N-methyl-aminocarbonylmethyl]-4-(dimethylaminocarbonyl)cinnamylamide hydrochlroide); WIN-64338 ([4-{(2[{bis(cyclohexylamino) methylene}amino]-3-[2-naphthyl]-1-oxopropyl) amino}phenyl]methyl) tributylphosphonium chloride monohydrochloride); WIN-62319; CP-2458; and others described in Abe et al., *J. Med. Chem.*, volume 41, pages 564–578 (1998) and Salvino et al., *J. Med. Chem.*, volume 36, pages 2583–2584 (1993); the entire content of the foregoing publications are incorporated herein by reference to the extent such publications disclose non-peptide BK antagonists of the present invention.

Examples of bissuccinimide-alkane peptide dimer BK antagonists of the present invention include CP-0127, CP-0364, and other compounds described in Cheronis et al, *J. Med Chem.*, volume 37, pages 348–355 (1994); *J. Med. Chem.*, volume 35, pages 1563–1572 (1992); and Srivastava et al., *Immunopharmacol.*, volume 33, pages 194–197 (1996); the entire contents of the foregoing publications are incorporated herein by reference to the extent such publications disclose non-peptide BK antagonists of the present invention.

Other examples of psuedopeptide BK antagonists of the present invention include NPC-18521, NPC-18688 and others described in Mavunkel et al., *J. Med Chem.*, volume 39, pages 3169–3172 (1996), the entire contents of which is incorporated herein by reference to the extent such publications discloses non-peptide BK antagonists of the present invention.

The non-peptide BK antagonists of the present invention may also be readily elucidated by employing the following bradykinin receptor and/or cellular functional assays:

Bradykinin receptor binding assays. Sharif and Whiting have described this type of receptor binding assay in: Sharif and Whiting, *Neurochemical Res.*, volume 12, pages 1313–1320 (1993); and Sharif and Whiting, *Neurochem. Internat.*, volume 18, pages 89–96 (1991), the entire contents of which are incorporated herein by reference, and which may be modified as described below, for the elucidation of non-peptide BK antagonists of the present invention. Briefly, cells (e.g., HSDM1C1, TM3 or CEPI-17-CL4) or tissues (e.g., guinea pig ileum, lung or brain) bearing the constitutive $B_2$-BK receptor or cells genetically engineered to express such receptors, are harvested and gently homogenized in 25 mM TES (N-Tris[hydroxymethyl]methyl-a-aminoethansulfonic acid) buffer (pH 6.8, containing 1 mM 1.10 phenanthroline and a mixture of various peptide inhibitors (140 $\mu$g/ml bacitracin, 1 $\mu$M captopril. 1 mM dithiothreitol and 0.1% bovine serum albumin) using a Polytron tissue disrupter (setting "3–5" for 5–8 seconds). The homogenates are centrifuged at 30,000×g (20 minutes at 4° C.) and the cell pellets gently dispersed in the above-described TES buffer (at 10–30 mg wet weight tissue/ml) for the binding assay. The resuspended cell or tissue pellet homogenates (400 $\mu$l aliquots) are incubated with 50 $\mu$l of various concentrations of the test unlabeled, non-peptide BK antagonist candidate (1 pM–10 $\mu$M final concentrations) or buffer and 50 $\mu$l of [$^3$H]-BK (0.5 nM final concentration) in polypropylene tubes at 23° C. for 90 minutes in order to reach equilibrium. Non-specific binding is determined using 10 $\mu$M unlabeled BK. The assay is terminated by rapid vacuum filtration on a Tomtec cell harvester through Wallac "B" glass fiber filters (pre-soaked in 0.3% polyethyleneimine) using three 3 ml ice-cold 50 mM Tris HCl buffer (pH 7.4) washes. Receptor-bound radioactivity captured on the filter is measured by liquid scintillation spectrometry on a Wallac Beta-scintillation counter. Data analysis is performed using a standard non-linear, iterative curve-fitting computer program to determine the affinity ($K_i$, defined as the concentration required to inhibit [$^3$]-BK binding by 50% and indicating the ability of the compound to bind to the receptor) of the BK antagonist for the BK receptor. BK antagonists having a $K_i \leq 1\times10^{-7}$M (i.e., affinity 24 100 nM) are within the non-peptide BK antagonist definition of the present invention.

Cellular functional assay. Sharif and Xu have described this type of functional assay in: Sharif and Xu, *Exp. Eye Res.*, volume 63, pages 631–637 (1996), the entire contents of which are incorporated herein by reference, and which may be modified as described below, for the elucidation of the BK antagonists of the present invention. Briefly, cells bearing the constitutive $B_2$-BK receptor (e.g., HSDM1C1, TM3 or CEPI-17-CL4) or cells genetically engineered to express such receptors are grown in sterile 24-well culture plates and are incubated with [$^3$H]-myo-inositol (2 $\mu$Ci/ml; 15–17 Ci/mmol) in sterile culture medium for 24 hours at 37° C. in order to label the cell membrane phosphoinositide lipids. The medium is then aspirated and the cells exposed to BK in sterile culture medium (15 mM HEPES buffer) containing 10 mM LiCl for 60 minutes at 37° C. in order to facilitate the accumulation of [$^3$H]-inositol phosphates ([$^3$H]-IPs) (Berridge et al., *Biochem. J.*, volume 206, pages 587–595 (1982)). To determine the potency and/or efficacy of a non-peptide BK antagonist candidate, the candidates are added (1 pM–10 $\mu$M final concentrations) to the cells 30 minutes prior to the addition of BK (e.g., 1 $\mu$M final concentration). The medium is aspirated at the end of the incubation, and the assay terminated by the addition of 1 ml of ice-cold 0.1M formic acid and the [$^3$H]-IPs quantified by standard ion exchange chromatography (Berridge et al. 1982) and liquid scintillation spectrometry on a beta-counter. Data analysis is performed using a standard non-linear, iterative curve-fitting computer program to determine the potency ($K_i$, defined as the concentration required to inhibit the BK-induced [$^3$H]-IPs accumulation by 50% and indicating the ability of the antagonist to block the agonist-induced functional response) of the BK antagonist for the BK receptor. BK antagonists with a $K_i \leq 1 \times 10^{-7}$ M (i.e. potency $\geq 100$ nM) are within the non-peptide BK antagonist definition of the present invention.

Preferred BK antagonists of the present invention are those antagonists which are: 1) potent BK antagonists; 2) relatively hydrophobic for topical uptake and rapid penetration; 3) non-labile; and 4) exhibit a low occurrence of side-effects. BK antagonists which inhibit the activation of the $B_2$ receptor are most preferred BK antagonists of the present invention. Examples of $B_2$ receptor antagonists include FR173657 ((E)-3-(6-acetamido-3-pyridyl)-N-[-[2,4-dichloro-3-[(2-methyl-8-quinolinyl) xymethyl]phenyl]-N methylaminocarbonylmethyl]acrylamide); FR167344 (N-[N-[3-[3-bromo-2-methylimdazo[1,2-a]pyridin-8-yl] oxymethyl]2,4-dichlorophenyl]N-methylaminocarbonylmethyl]4-(dimethylaminocarbonyl) cinnamylamide hydrochlroide); WIN-64338 ([4-{(2[{bis (cyclohexylamino)methylene}amino]-3-[2-naphthyl]-1-oxopropyl)amino}phenyl]methyl) tributylphosphonium chloride monohydrochloride); WIN-62318, CP-2458, CP-0127, CP-0364, NPC-18521 and NPC-18688.

The BK antagonists of the present invention are useful in lowering intraocular pressure and thus are useful in the treatment of ocular hypertension or glaucoma. As used herein, the term "pharmaceutically effective amount" refers to that amount of one or more BK antagonist(s), which controls IOP when administered to a mammal. As used herein, the word "controls," as used in the previous sentence, refers to lowering IOP or stabilizing IOP, i.e., preventing an increase in IOP. The compounds of the present invention can be administered as solutions, suspensions, or emulsions (dispersions) in a suitable ophthalmic vehicle. The preferred route of administration is topical.

In preparing present invention compositions for topical administration, the BK antagonists are generally formulated from about 0.00005 to about 0.5 percent by weight (wt %). The BK antagonists are preferably formulated between about 0.0003 to about 0.3 wt % and, most preferably, between about 0.0005 and about 0.03 wt %. In general, the compositions will be solutions, having a pH between 4.5 to 7.4. While the precise regimen is left to the discretion of the clinician, the resulting solution or solutions are preferably administered by placing one drop of each solution(s) in each eye one to four times a day, or as directed by the clinician.

Other ingredients which may be desirable to use in the ophthalmic preparations of the present invention include preservatives, co-solvents, buffers, viscosity building agents and penetration enhancers. Viscosity building agents, such as hydroxymethyl cellulose, hydroxyethyl cellulose, methylcellulose, polyvinylpyrolidine, or the like, may be added to the compositions of the present invention to improve the retention of the compound in the conjunctival sac or surrounding area. In order to prepare a sterile ophthalmic ointment formulations, the BK antagonist may be combined with a preservative in an appropriate vehicle, such as white petroleum, mineral oil or liquid lanolin. Sterile ophthalmic gel formulations may be prepared by suspending the BK antagonist in a hydrophilic base prepared from the combination of, for example, carbopol-940, or the like, according to the methods known in the art for other ophthalmic formulations. Other compositions of the resent invention may contain penetration enhancing agents such as cremephor and tween 80, in the event the BK antagonists are less penetrating in the eye.

As used herein, the term "pharmaceutically acceptable ophthalmic vehicle" refers to those vehicles which cause at most, little to no ocular irritation, provide suitable preservation if needed, and deliver one or more BK antagonists of the present invention in a homogenous dosage.

Preferred formulations of BK antagonists of the present invention include the following Examples 1–4:

EXAMPLE 1

| Ingredient | Amount (wt %) |
| --- | --- |
| BK antagonist | 0.001 |
| Phosphate Buffered Saline | 1.0 |
| Benzalkonium Chloride | 0.01 |
| Polysorbate 80 | 0.5 |
| Purified water | q.s. to 100% |

EXAMPLE 2

Example of a preferred BK antagonist composition of the present invention:

| Ingredient | Amount (wt %) |
| --- | --- |
| BK antagonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 3

Example of a preferred BK antagonist composition of the present invention:

| Ingredient | Amount (wt %) |
|---|---|
| BK antagonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 4

| Ingredient | Amount (wt %) |
|---|---|
| BK antagonist | 0.0005 |
| Phosphate Buffered Saline | 1.0 |
| Hydroxypropyl-β-cyclodextrin | 4.0 |
| Purified water | q.s. to 100% |

I claim:

1. A method for controlling intraocular pressure and/or treating glaucoma which comprises administering topically to the eye a composition comprising a therapeutically effective amount of a non-peptide bradykinin antagonist in a pharmaceutically acceptable ophthalmic vehicle.

2. A method of claim 1, wherein the non-peptide bradykinin antagonist is selected from the group consisting of FR173657 ((E)-3-(6-acetamido-3-pyridyl)N-[N-[2,4-dichloro-3-[(2-methyl-8-quinolinyl)oxymethyl]phenyl]-N-methylaminocarbonyl methyl]acrylamide); FR167344 (N-[N-[3-[3-bromo-2-methylimdazo[1,2-a]pyridin-8-yl)oxymethyl]2,4-dichlorophenyl]N-methyl-aminocarbonylmethyl]-4-(dimethylamino carbonyl) cinnamylamide hydrochlroide); WIN-64338 ([4-{(2[{bis (cyclohexyl amino)methylene}amino]-3-[2-naphthyl]-1-oxopropyl)amino}phenyl]methyl)tributyl phosphonium chloride monohydrochloride); WIN-62318, and/or combinations thereof.

3. The method of claim 2 wherein the non-peptide BK antagonist is FR173657 ((E)-3-(6-acetamido-3-pyridyl)-N-[N-[2,4dichloro-3-[(2-methyl-8-quinolinyl)oxymethyl]phenyl]-N-methylaminocarbonylmethyl]acrylamide).

4. The method of claim 1, wherein the non-peptide BK antagonist is elucidated using a bradykinin receptor antagonist assay or a cellular functional assay.

5. The method of claim 1, wherein the non-peptide BK antagonist is a $B_1$-BK antagonist.

6. The method of claim 1, wherein the non-peptide BK antagonist is a $B_2$-BK antagonist.

7. The method of claim 1, wherein the non-peptide BK antagonist is a $B_3$-BK antagonist.

8. The method of claim 1, wherein the non-peptide BK antagonist is a $B_4$-BK antagonist.

* * * * *